United States Patent
Paulk, Jr. et al.

(10) Patent No.: US 11,198,051 B2
(45) Date of Patent: Dec. 14, 2021

(54) SYSTEM AND METHOD FOR DETECTING LOWER BODY POSITIONS, MOVEMENTS, AND SEQUENCE IN GOLF SWING TRAINING

(71) Applicant: PD Golf LLC, a Texas limited liability company, Dallas, TX (US)

(72) Inventors: James R. Paulk, Jr., Dallas, TX (US); Sumitrajit Dhar, Wilmette, IL (US)

(73) Assignee: PD Golf LLC, Dallas, TX (US)

(*) Notice: Subject to any disclaimer, the term of this patent is extended or adjusted under 35 U.S.C. 154(b) by 345 days.

(21) Appl. No.: 16/257,753

(22) Filed: Mar. 4, 2019

(65) Prior Publication Data
US 2020/0238149 A1 Jul. 30, 2020

(51) Int. Cl.
A63B 69/36 (2006.01)
A63B 71/06 (2006.01)

(52) U.S. Cl.
CPC ...... *A63B 69/3608* (2013.01); *A63B 69/3667* (2013.01); *A63B 2069/367* (2013.01); *A63B 2071/0625* (2013.01)

(58) Field of Classification Search
CPC ............ A63B 69/3608; A63B 69/3667; A63B 2071/0625; A63B 2069/367; G06K 9/00342; G09B 19/0038
USPC ......... 473/269, 213, 215; 474/252; 434/247, 434/252
See application file for complete search history.

(56) References Cited

U.S. PATENT DOCUMENTS

| | | | |
|---|---|---|---|
| 4,577,868 A | 3/1986 | Kiyonaga | |
| 4,813,436 A * | 3/1989 | Au | A61B 5/1038 356/620 |
| 5,111,410 A * | 5/1992 | Nakayama | A61B 5/1127 348/157 |
| 5,118,112 A | 6/1992 | Bregman et al. | |
| 5,372,365 A | 12/1994 | McTeigue et al. | |
| 5,419,562 A * | 5/1995 | Cromarty | A63B 24/0003 434/247 |
| 5,511,789 A | 4/1996 | Nakamura | |
| 5,697,791 A * | 12/1997 | Nashner | A63B 24/0003 434/247 |
| 6,001,023 A | 12/1999 | Sanchez et al. | |
| 6,050,963 A * | 4/2000 | Johnson | A61B 5/1124 600/587 |

(Continued)

FOREIGN PATENT DOCUMENTS

CA 2698078 A1 9/2011

*Primary Examiner* — Nini F Legesse
(74) *Attorney, Agent, or Firm* — Thomas Horstemeyer LLP

(57) ABSTRACT

Disclosed are various embodiments of golf training device that helps a golfer learn and coordinate lower body positions and movements with upper body movements, using a series of feedback signals. In one embodiment, a system comprises a foot sensor that attaches to a Lead Foot of a user. The foot sensor is configured to detect a heel of the Lead Foot being raised. The system also comprises a leg sensor that attaches to a Trail Knee of the user, and the leg sensor detects a bend in a knee of a Trail Leg of the user after detecting the heel being raised. The foot sensor is configured to detect the heel being lowered at an instance after the detection of the bend in the knee of the Trail Leg and while the knee remains bent. The system further comprises a feedback device configured to activate feedback indicators.

20 Claims, 5 Drawing Sheets

(56) References Cited

U.S. PATENT DOCUMENTS

| | | | |
|---|---|---|---|
| 6,778,866 B1 * | 8/2004 | Bettwy | A63B 24/0006 434/247 |
| 7,376,245 B2 * | 5/2008 | Morozumi | A63B 24/0003 382/103 |
| 7,527,561 B2 | 5/2009 | Jang et al. | |
| 7,857,708 B2 * | 12/2010 | Ueda | A63B 24/0021 473/257 |
| 7,905,796 B2 | 3/2011 | Papa, Jr. | |
| 8,043,173 B2 | 10/2011 | Menalagha et al. | |
| 8,864,597 B2 | 10/2014 | Kim et al. | |
| 8,896,626 B2 * | 11/2014 | Kawai | G11B 27/034 345/629 |
| 8,990,054 B1 * | 3/2015 | Ketterling | G09B 19/0038 703/2 |
| 9,254,430 B2 | 2/2016 | LaSala | |
| 9,827,478 B1 | 11/2017 | Najafi et al. | |
| 9,907,997 B2 | 3/2018 | Cusey et al. | |
| 10,307,640 B2 * | 6/2019 | Mooney | G06K 9/00342 |
| 10,383,550 B2 * | 8/2019 | Hyde | A61B 5/1121 |
| 10,661,143 B2 * | 5/2020 | Stahl | A63B 69/3667 |
| 2003/0017883 A1 | 1/2003 | Yoshiike | |
| 2003/0054327 A1 | 3/2003 | Evensen | |
| 2006/0194178 A1 | 8/2006 | Goldstein | |
| 2009/0227386 A1 | 9/2009 | Whitaker | |
| 2010/0075806 A1 * | 3/2010 | Montgomery | A63B 24/0006 482/8 |
| 2010/0227738 A1 * | 9/2010 | Henderson | A63B 24/0006 482/8 |
| 2010/0283630 A1 * | 11/2010 | Alonso | H04Q 9/00 340/870.11 |
| 2011/0304497 A1 * | 12/2011 | Molyneux | A63B 24/0021 342/42 |
| 2012/0322570 A1 | 12/2012 | Allen | |
| 2013/0171596 A1 * | 7/2013 | French | G09B 19/00 434/236 |
| 2016/0335913 A1 | 11/2016 | Grant et al. | |
| 2017/0189751 A1 * | 7/2017 | Knickerbocker | G09B 19/0038 |
| 2019/0046857 A1 * | 2/2019 | Sellers, III | A63B 69/0026 |

* cited by examiner

SYSTEM AND METHOD FOR DETECTING LOWER BODY POSITIONS, MOVEMENTS, AND SEQUENCE IN GOLF SWING TRAINING

BACKGROUND

Golf is a popular sport that people all over the world enjoy. Golf participants enjoy the challenge of consistently executing a proper golf swing. In many cases, golf participants consider the challenge of learning to consistently execute a proper golf swing to be a big part of developing into a skilled player. Oftentimes, golfers are taught to focus on upper body elements, such as a particular hand grip, arm movement, and shoulder movement, in order to execute a consistent golf swing.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Golf is a popular but challenging sport currently being played by many today. Part of the difficulty in golf involves being able to consistently execute a playable golf swing. The present disclosure relates to various embodiments of a golf training device which teaches use of the lower body and coordination of the lower body with the upper body during a golf swing. Specifically, the embodiments of the golf training device teach coordination of lower body movements during a backswing and during the transition into a downswing of a golf swing. During the execution of a golf swing, the embodiments of the golf training device can teach a proper sequence of lower body positions and movements by way of a series of progressive feedback signals that are sequentially activated by sensors in real-time or substantially real-time.

As an example, a golfer may first determine an imaginary line extending from his or her golf ball to an intended target, which may represent a target line. The golfer may position his or her body with the toes touching a line parallel to the target line, where the golfer is positioned at the proper distance to address the ball in preparation for the swing. The golfer's foot, heel, knee, leg, and hip closest to the target are the Lead Foot, Lead Heel, Lead Knee, Lead Leg, and Lead Hip. The other side of the golfer may be considered as being the Trail Foot, Trail Heel, Trail Knee, Trail Leg, and Trail Hip.

In some example implementations, the embodiments of the golf training device may track the movement of the Lead Heel and the Trail Knee of a golfer to encourage the proper transfer of weight during a golf swing. Movement indicators can be used to identify a transfer of weight to the Trail Leg and Trail Hip during the backswing, whether the weight is being maintained on the Trail Leg and Trail Hip during the backswing, and a transfer of weight forward led by the Lead Heel, Lead Leg, and Lead Hip during a transition into a downswing. Particularly, in one example, a proper sequence of golf swing movement may include detecting a first state of a raised heel of the Lead Foot, a second state of a bent knee of the Trail Leg and while the heel of the Lead Foot is still elevated, and a third state of the heel of the Lead Foot being lowered while the knee of the Trail Leg is still bent. The third state is where the train of movements of downswing begins. The embodiments of the golfing training device can be used to detect and provide feedback indications for other sequences of movements for a golf swing. In the following discussion, a general description of the system and its components is provided, followed by a discussion of the operation of the same.

Figure 1A:
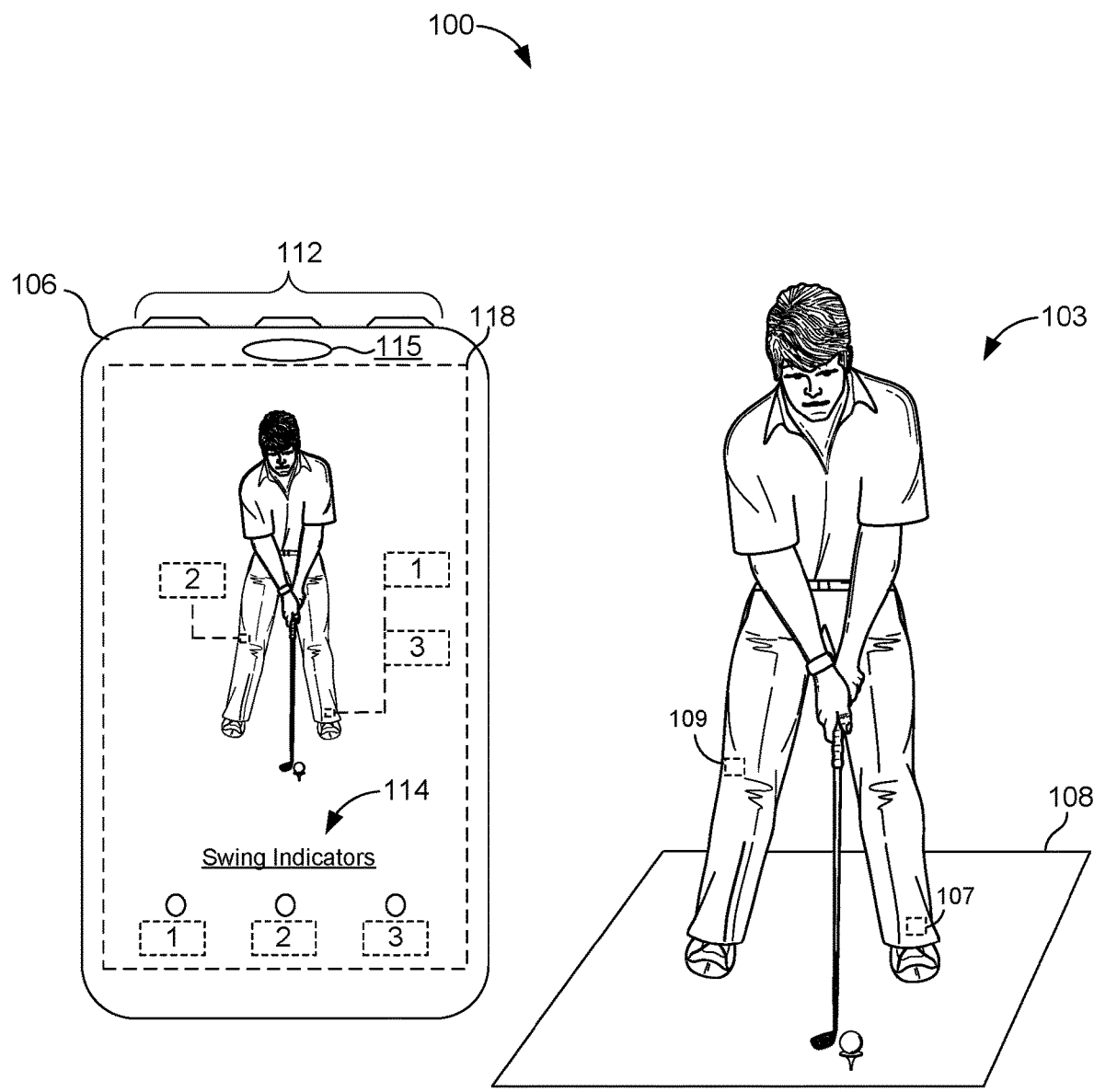
FIG. 1A is a drawing of an example feedback sensing system, according to an embodiment described herein.

Beginning with FIG. 1A, shown is a pictorial drawing of a feedback sensing system 100 and a golfer. In some non-limiting examples, the feedback sensing system 100 may be used to track and provide feedback indicators for a proper sequence of movements during a golf swing. The feedback sensing system 100 may include a sensing system 103 and a feedback device 106. The sensing system 103 may comprise a foot sensing device 107 and a leg sensing device 109. The sensing system 103 may be used to detect and/or track the movements of various body parts of the golfer, such as foot movement, leg movement, knee movement, hip movement, and movement of other body parts involved in a golf swing. The sensing system 103 may include various components in a wired system, a wireless system, or some combination a wired and a wireless system. In FIG. 1A, the sensing system 103 is illustrated as a wireless system where the foot sensing device 107 and the leg sensing device 109 are capable of wireless communication with each other and the feedback device 106. In FIG. 1A, the example feedback device 106 is shown capturing video of a golfer executing a swing.

The foot sensing device 107 may be used to detect and track various movements of different areas of a foot of the golfer. For example, the foot sensing device 107 may be used to detect movements related to the heels, the ankles, the toes and other suitable areas of the foot. The foot sensing device 107 may comprise one or more sensors, such as a position sensor, a switch, a pressure sensor, and other suitable devices to foot movement. A sensor may be configured to indicate different foot positions during a golf swing. For instance, a sensor may be used to indicate different foot states, positions, orientations, rotations, or other foot positions. In one example, a first state may represent a detection of a heel of the Lead Foot being raised. A second state may represent a detection of the heel of the Lead Foot being lowered at an instance after the detection of the first state. In some embodiments, the foot sensing 107 is embedded in or on an indoor or outdoor floor mat 108.

The leg sensing device 109 may be used to detect and track various movements of different areas of the leg of a golfer. For example, the leg sensing device 109 may be used to detect movements related to the calf, knee, quadriceps, or other leg movements. The leg sensing device 109 includes one or more sensors, such as a position sensor, a flex sensor, a switch, and other suitable device to detect certain movement by the leg of the golfer. For the leg sensing device 109, one or more sensors can be used to detect a degree of bending or flexing of the Trail Leg of the golfer. To this end, the leg sensing device 109 can determine an instance in which the weight of the golfer is being transferred. For example, when the first state of the food sensing device 107 detects the heel of the Lead Foot being raised, the leg sensing device 109 can detect instances when weight is being transferred to the Trail Leg.

In some embodiments, a degree of knee bend or a magnitude of flexion of the knee can be used to identify a particular state of a golf swing. As a non-limiting example, the degree of knee bend or the magnitude of flexion at the knee can be used to indicate that a second state of the golf swing has been achieved. In one non-limiting example, the leg application 228 and/or the feedback application 231 can be used to detect an initial degree of bend, which represents a bend of the knee for a golfer in his or her initial instance before an execution of a swing. In some cases, the initial degree of bend or magnitude of flexion can automatically be detected and determined from the leg sensor 219 and the leg application 228 as the golfer settles into his or her initial golf stance. In this instance, the golfer may have to hold his or her initial golf stance for a period of time in order for the leg sensing device 109 to detect the initial degree of bend. As a non-limiting example, before initiating the golf swing, the feedback device 106 may prompt the golfer to hold his or her initial golf stance for three seconds after a visual or audible signal. The three seconds may provide time for the sensing system 103 to assess the initial degree of bend before the golfer initiates the golf swing. The visual or audible signal may be initiated after the golfer has manipulated a switch to initiate a swing detection process.

In other cases, the leg sensor 219 and the leg application 338 can determine an initial degree of bend after monitoring a series of golf swings. In another case, the initial degree of knee bend can be entered via a user interface on the feedback device 106. In some non-limiting examples, the sensing system 103 may omit the detection or determination of an initial degree of bend for an initial posture of a golfer. In other words, the sensing system 103 can use thresholds for detecting a knee bend, a raised heel, and a lowering of the heel without determining an initial posture of the golfer before a swing is performed.

In some embodiments, the feedback sensing system 100 may have a variety of techniques that enable a golfer to signal that he or she has addressed the golf ball and is about to initiate a golf swing. Initially, the feedback sensing system 100 may detect power being applied as a result of a power switch. The feedback sensing system 100 may first operate in a ready mode after being powered on. In some scenarios, the entire portion or parts of the feedback sensing system 100 may be in a standby or power-conserving mode of operation and subsequently move to the ready mode after a user has manipulated a switch, such as a ready switch. The ready switch may be used for signaling that a golfer is presently in his or her golf stance and about to initiate a golf swing. As a result, the ready switch and ready mode can enable the feedback sensing system 100 to ignore body movements taking place that are not related to a golf swing, such as a golfer walking around. In other cases, the feedback sensing system 100 can be placed in the standby mode after a partial golf swing attempt with respect to a time out period or after the completion of a golf swing.

The ready switch may be a momentary switch, a position switch, a pressure switch, a contact switch, or other suitable device. The ready switch may be located on the floor mat 108, the feedback device 106, the sensing system 103, or other appropriate locations. For example, in some cases, the ready switch may be incorporated into the floor mat 108. The golfer may be able to physically manipulate the ready switch by hand or with a golf club. In these scenarios, the ready switch can be mechanically, electrically, or wirelessly in communication with the other components of the sensing system 103 in the floor mat 108. Particularly, the ready switch can transmit a ready signal to the other components of the sensing system 103 and the feedback device 106 in preparation for a swing detection sequence.

In other examples, the ready switch may be a portable device that is located on the golfer, such as being attached to a golf glove, a shirt, a shoe, a pair of pants, golf shorts, a golf skirt, a belt, or other apparel items. The ready switch may also be incorporated into other portable devices such as a smartphone, a watch, an activity tracker, a headset, or other suitable portable devices. These portable embodiments of the ready switch may wirelessly communicate to the sensing system 103 that a golfer has addressed the ball and prepared to initiate a golf swing. In these examples, the ready switch may transmit a ready signal to the feedback device 106 and/or the sensing system 103 in preparation for a swing detection sequence.

In another example, the foot sensing device 107 and/or the leg sensing device 109 can be physically tapped one or more times to indicate that the golfer is about to initiate a golf swing. For example, the golfer may tap his or her heel two times against the ground to activate the feedback sensing system 100 in preparation for a golf swing. The sensing system 103 may also have a power switch for turning the sensing system 103 on and off.

Additionally, a range of bend at the knee can be set with respect to the initial degree of bend at the knee via a user interface on the feedback device 106. In some cases, the leg application 228 and/or the feedback application 231 can generate a recommended range of bend based on various factors, such as previous swing data for the golfer, the physical attributes of the golfer (e.g., height, weight), and other suitable factors. In some embodiments, the range of bend at the knee can be represented as a degree of bend threshold. The range of bend can represent the amount of bend that needs to occur from the initial degree of knee bend in order to indicate that the knee of the Trailing Leg is sufficiently bent for a second state of the golf swing. For example, an initial degree of bend at the knee for a golfer in his or her initial stance can be fifteen degrees and the range of bend can be set for ten degrees. After the golf meets or exceeds twenty-five degrees of bend at the knee of the Trailing Leg during a swing, the leg application 228 and/or the feedback application 231 may indicate that the second state of the golf swing has been achieved. The second state detection may also be based on the first state being detected prior, which may represent the detection of a raised heel of the Lead Foot. The initial degree of bend and the range of bend can vary from golfer to golfer and, in the case of a single golfer, can vary with the progression of the golfer's level of skill. Additionally, the initial degree of bend and the range of bend can be adjusted to accommodate the different physical attributes and swing preferences of a golfer.

The feedback device 106 may be used to generate one or more feedback signals after the detection of certain movements by the sensing system 103. The feedback device 106 may generate feedback signal that are aural, visual, tactile, or a combination. In FIG. 1A, the feedback device 106 is depicted as being in wireless communication with the sensing system 103. FIG. 1A also illustrates that the feedback device 106 includes visual indicators 112, a speaker 115, and a display 118. FIG. 1A illustrates that the feedback device 106 may have a camera that is used to capture images and/or video of a golfer executing a swing. As shown on the display 118, the images and/or video may be used to detect the movement of different body members of the golfer during a swing.

FIG. 1A illustrates that the feedback device 106 includes multiple visual indicators 112, which may be light emitting diodes (LEDs), light bulbs, or some other suitable visual indicator. Each visual indicator 112 can be activated after receiving an indication from the sensing system 103 of a proper detected movement. As a non-limiting example, a first visual indicator 112 can be illuminated after the sensing system 103 detects a heel of a Lead Foot of the golfer has been raised. A second visual indicator 112 can be illuminated after the sensing system 103 detects that both the Trail Knee of the golfer is bent and the heel of the Lead Foot is still raised. After the second visual indicator 112 has been activated, a third visual indicator 112 can be illuminated after the sensing system 103 detects that the heel of the Lead Foot has begun to move downward while the Trail Knee is still bent. Accordingly, the visual indicators 112 can be activated to provide visual verification of that the positions and movements of the golfer's lower body have occurred in the proper sequence of the backswing and initiation of the downswing. Likewise, the speaker 115 can be used to generate audible sounds corresponding with each stage of a swing in the proper sequence.

In another example scenario, the feedback device 106 can be used to capture video of a golfer executing a golf swing. As the golfer executes the swing, the feedback device 106 can illuminate swing indicators 114 on the display 118 as each stage of the swing is performed. In some embodiments, the feedback device 106 may use image processing algorithms to detect the movement of various body parts, such as movements related to the heel, ankle, knee, leg, quadriceps, calf, or other body parts. The captured video can be replayed with the swing indicators 114 displayed when the detect movements occurred.

In one scenario, the feedback device 106 can use image processing algorithms to detect a heel being raised by a Lead Foot, a bent knee of the Trail Leg, and the heel of the Lead Foot being lowered without the use of the sensing system 103. The image processing algorithms may use behavioral models to represent a raised heel, a lowering heel, a bent knee, and other swing movements. The behavioral model may include video frame data of frames depicting a frame-by-frame progression of a raised heel, a bent knee, and other swing movements. The behavioral models can also be used to calculate a degree of bend in at the knee. The degree of bend at the knee can also refer to a magnitude of flexion at the knee.

In this scenario, the feedback device 106 can activate the visual indicators 112 and/or audible sounds from the speaker 115 in real-time as each stage is detected by way of a camera associated with the feedback device 106. In another scenario, the feedback device 106 can use image processing algorithms to detect a heel being raised by a Lead Foot, a bent knee of the Trail Leg, and the heel of the Lead Foot being lowered with the use of sensing system 103. In this scenario, the sensing system 103 can facilitate tracking movements of body parts by way of various object detection algorithms. Further, the sensing system 103 may generate timestamps individually related to the occurrence of the detection of a heel being raised by a Lead Foot, the detection of a bent knee for the Trail Leg, and the detection of the heel of the Lead Foot being lowered. The timestamps can be correlated with video captured of the golf swing. The swing indicators 114 can be added to the captured video to illustrate when each swing indicator 114 was detected.

Figure 1D:
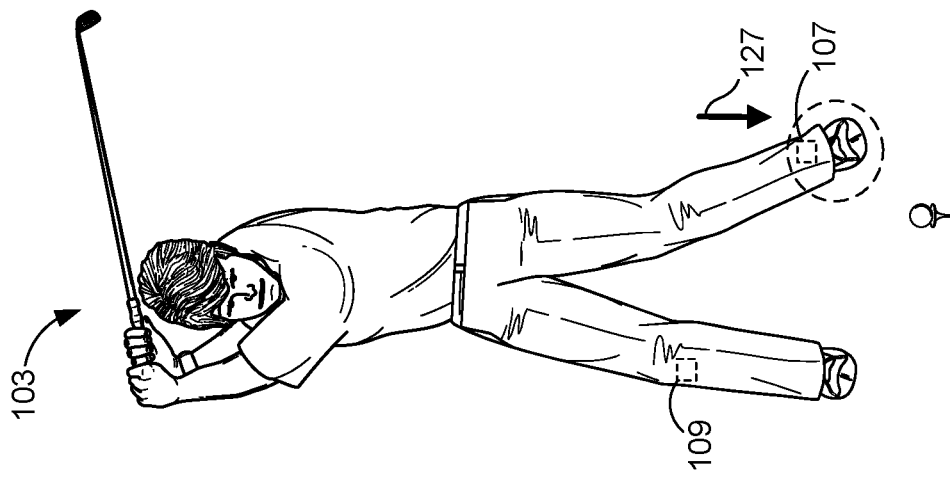
FIGS. 1B through 1D are drawings illustrating different stages of an example golf swing monitored by the feedback sensing system in FIG. 1A, according to an embodiment described herein.
Figure 1C:
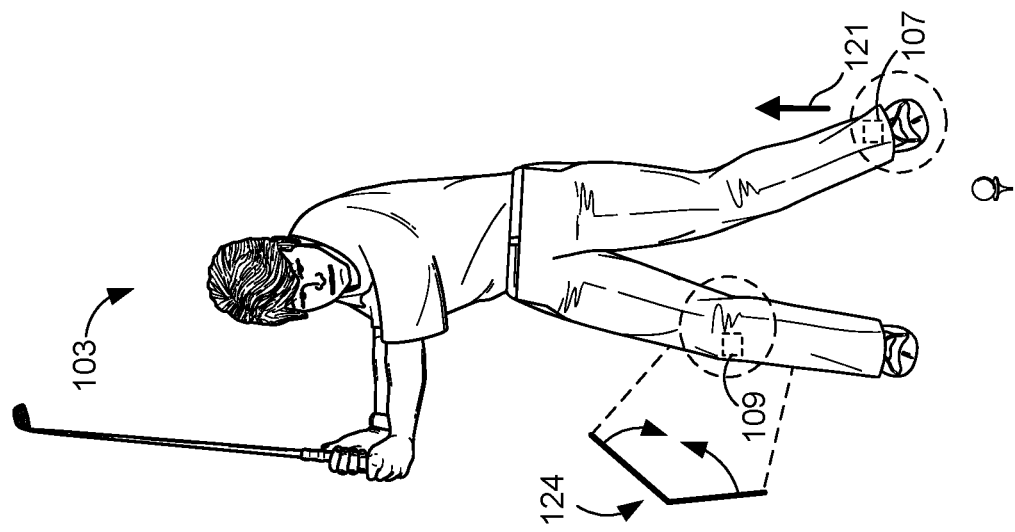
Figure 1B:
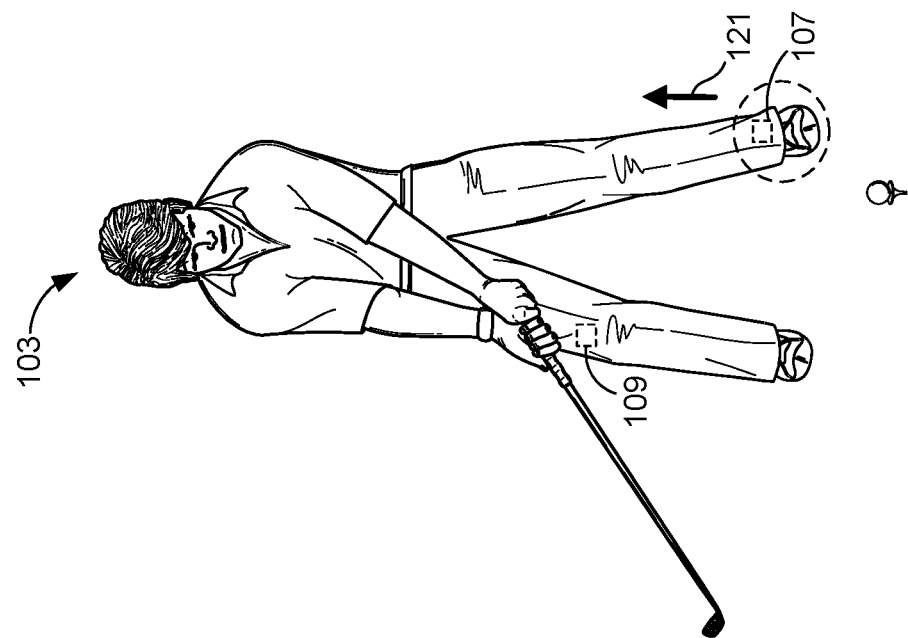

Referring next to FIGS. 1B through 1D, shown are a series of drawings of a golfer executing a sequence of a golf swing at different stages. FIG. 1A illustrates a golfer in an initial stance, where the ball has been addressed. FIGS. 1B through 1D illustrate the remaining stages of the golf swing after FIG. 1A. The feedback sensing system 100 can be used to detect particular movements at each stage of a golf swing.

In FIG. 1B, the golfer initiates a backswing of the golf club. As the golfer brings the club back, the golfer lifts the heel of his or her Lead Foot. In FIG. 1B, reference 121 indicates that the sensing system 103 detects an upward movement of the heel of the Lead Foot. At this stage, the sensing system 103 can generate a first feedback signal to the feedback device 106. After receiving the first feedback signal, the feedback device 106 can activate the first visual indicator 112. The activation of the first visual indicator 112 provides a visual and/or audible confirmation for the golfer that he or she properly executed the first step in a golf swing.

In FIG. 1C, the golfer continues with the backswing by bringing the club further around and upward and transferring weight to the Trail Leg. When the backswing begins and as weight is shifted to the Trail Leg, the sensing system 103 may detect a degree of bend in the knee of the Trail Leg that meets or exceeds a degree threshold, as indicated by reference 124. In some examples, the sensing system 103 can generate a second feedback signal to the feedback device 106. In this example, the feedback device 106 activates a second visual indicator 112 after receiving the second feedback signal and if the first feedback signal is still active. Accordingly, the feedback device 106 ensures that the heel on the Lead Foot is raised first. Then, the feedback device 106 ensures that the knee on the Trail Leg remains bent while the heel of the Lead Foot remains raised.

In FIG. 1D, the golfer transitions from a backswing to initiate a downswing toward the ball. At this stage, the sensing system 103 may detect the raised heel moving downward, as indicated by reference 127. The downward movement of the heel represents a commencement of the transfer of the weight from the Trail side to the Lead side of the golfer. The sensing system 103 can transmit a third feedback signal to the feedback device 106. The feedback device 106 can activate a third visual indicator 112 but only if the first feedback signal and the second feedback signal are still active. This indicates that the Lead FootTrail Knee was bent while the heel of the Lead Foot was detected moving downward.

Figure 2:
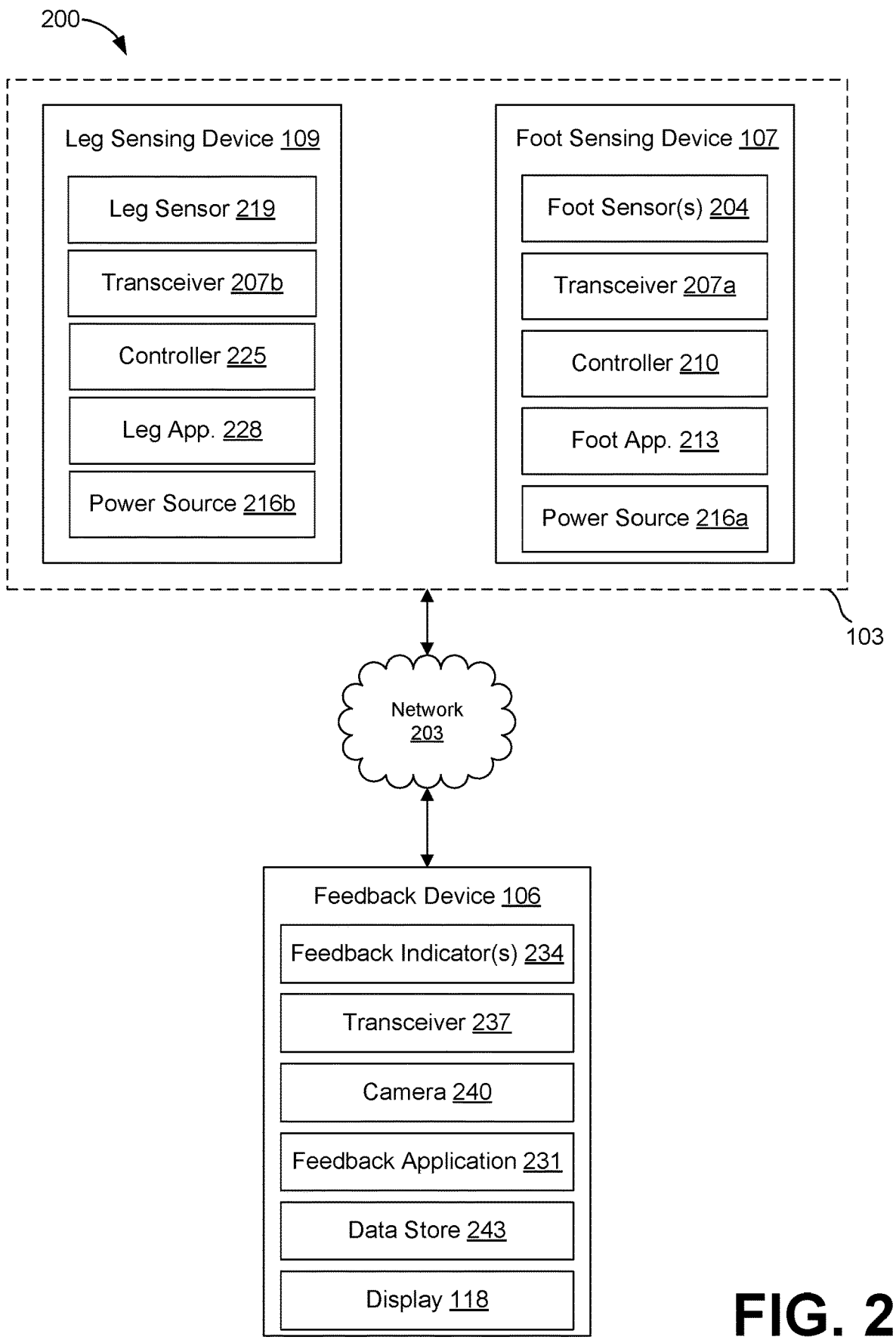
FIG. 2 is a drawing of a network environment for the feedback sensing system from FIG. 1A, according to an embodiment described herein.

With reference to FIG. 2, shown is a networked environment 200 according to various embodiments. The networked environment 200 includes a sensing system 103 and a feedback device 106, which are in data communication with each other via a network 203. The network 203 includes wide area networks (WANs) and local area networks (LANs). These networks can include wired or wireless components or a combination thereof. Wired networks can include Ethernet networks, cable networks, fiber optic networks, and telephone networks such as dial-up, digital subscriber line (DSL), and integrated services digital network (ISDN) networks. Wireless networks can include cellular networks, satellite networks, Institute of Electrical and Electronic Engineers (IEEE) 802.11 wireless networks (i.e., WI-FI®), BLUETOOTH® networks, microwave transmission networks, as well as other networks relying on radio broadcasts. The network 203 can also include a combination of two or more networks 203. Examples of networks 203 can include the Internet, intranets, extranets, virtual private networks (VPNs), and similar networks.

The sensing system 103 may be used to detect and/or track the movements of various locations on the golfer, such foot movement, leg movement, knee movement, hip movement, and other suitable locations on a golfer. The sensing system 103 may include various components in a wired system, a wireless system, or a combination of components from the wired system and the wireless system. The sensing system 103 comprises a foot sensing device 107 and a leg sensing device 109.

The foot sensing device 107 may be used to detect and track various movements of different areas of a foot of the golfer. For example, the foot sensing device 107 may be used to detect heel, ankle, toe and other suitable foot movements. The foot sensing device 107 may comprise a foot sensor 204, a transceiver 207a, a controller 210, a power source 216, and other suitable electronic components. In some cases, the foot sensing device 107 may be attached to a shoe or embedded within a shoe. The foot sensing device 107 may also be attached to an apparel item, such as a sock or a pair of pants. In other cases, the foot sensing device 107 may be a floor mat upon which the golfer stands while executing a golf swing.

The foot sensor 204 may comprise a switch, such as a momentary switch, a position sensor, a pressure sensor, a gyroscope sensor, a proximity sensor, an accelerometer, and other suitable sensors for detecting movements in various areas of the foot. In FIG. 2, the foot sensor 204 may represent one or more sensor devices. For example, a first foot sensor 204 may be positioned at a first location on the foot and a second foot sensor 204 may be positioned at a second location of the foot. The two foot sensors 204 can provide sensor data at their respective locations, which can facilitate determining the orientation of the foot.

The transceiver 207a, 207b may be a device for communicating data with other devices in the network environment 200 via wired communication, wireless communication, or some combination of the communication methods. The transceivers 207a, 207b may enable the foot sensor 204 and the leg sensor to be in data communication with each other and the feedback device 106. The transceivers 207a, 207b can be used to communicate sensor data, feedback signals, and detected movements related to the golfer.

In some embodiments, a foot sensor 204 may be configured to detect and communicate one or more states. For example, the foot sensor 204 can communicate a first state that represents the detection of a heel of a foot being raised to such a degree that it meets a height threshold. The foot sensor 204 may also communicate a second state that represents the detection of a heel of a foot being moving downward from its raised position. In other embodiments, the amount of pressure being applied to the ground can be detected. The foot sensing device 107 can determine whether the applied pressure meets a threshold for a participate state, such as raising a heel of a foot, lowering a heel of the foot, and other suitable movements for the foot.

The controller 210 may be a computing device that controls operations of the foot sensing device 107. The controller 210 can execute software applications on the foot sensing device 107. The controller 210 can also control and communicate with other components associated with the foot sensing device 107. For example, the controller 210 may be processor, microcontroller, a processing core, a computing modules, and other processing devices.

The foot application 213 can be executed by the controller 210. The foot application 213 can be executed to collect feedback data from the foot sensor 204 and communicate the feedback data to the leg sensing device 109, the feedback device 106, and/or other devices. In some embodiments, the foot application 213 can analyze the feedback data for determining a movement state of the golfer.

The power source 216a, 216b may include a battery, a recharging circuit, a power adapter, an energy harvesting circuit, and other suitable power components. In some embodiments, a battery and/or a recharging circuit may be included in the foot sensing device 107 to allow for the device to be portable. In other embodiments, the power source 216 may use an energy harvesting circuit to harvest energy and store the energy in the battery. The energy harvesting circuit may involve generating electrical energy after being activated from motion, heat, mechanical force, and from other suitable means.

The leg sensing device 109 may be used to detect and track various movements of different areas of the leg and hip of a golfer. For example, the leg sensing device 109 may be used to detect movements related to the calf, the knee, the quadriceps, the gluteus, and other suitable areas of a leg and hip. The leg sensing device 109 may include one or more leg sensors 219, a transceiver 207b, a controller 225, and the power source 216b.

The leg sensor 219 may be a position sensor, a flex sensor, or other suitable device to detect certain movement or position by the leg of the golfer. For the leg sensing device 109, one or more sensors can be used to detect movement of the leg and a degree of bend in the leg of the golfer. For example, a first leg sensor 219 may be positioned below the knee, and a second leg sensor 219 may be positioned above the knee. The two leg sensors 219 can provide sensor data with respect to their location, which can determine an orientation or a degree of bend/flex in the leg. The leg sensor 219 can be configured to generate a feedback signal after a certain degree of in the leg has been met or exceeded.

The controller 225 may be a computing device that controls operations of the leg sensing device 109. The controller 225 can execute software applications on the leg sensing device 109. The controller 225 can also control and communicate with other components associated with the leg sensing device 109. For example, the controller 225 may be a processor, a microcontroller, a processing core, a computing module, and other processing devices.

The leg application 228 can be executed by the controller 225. The leg application 228 can be executed to collect feedback data from the leg sensor 219 and communicate the feedback data to the foot sensing device 107, the feedback device 106, and/or other devices. In some embodiments, the leg application 228 can analyze the feedback data to a movement state of the golfer.

The feedback device 106 may be representative of one or more client devices coupled to the network 203. The feedback device 106 may comprise, for example, a processor-based system such as a computer system. Such a computer system may be embodied in the form of headphones, earbuds, a television, a smart speaker, a desktop computer, a laptop computer, personal digital assistants, cellular telephones, smartphones, music players, web pads, tablet computer systems, game consoles, electronic book readers, head mounted displays, voice interface devices, a media device, or other devices. The feedback device 106 may also include a display 118. The display 118 may include, for example, one or more devices such as liquid crystal display (LCD) displays, gas plasma-based flat panel displays, organic light emitting diode (OLED) displays, electrophoretic ink (E ink) displays, LCD projectors, or other types of display devices.

The feedback device 106 may include feedback indicators 234, a transceiver 237, a camera 240, and a data store 243. The feedback indicator 234 is generated to provide a golfer with confirmation that they executed a particular predefined movement at an appropriate time within a sequence of movements. The feedback indicator 234 can be used to include visual indicators, audible indicators, tactile indicators, or some combination. The visual indicators may include light bulbs, light emitting diodes (LEDs), or other visual indicators. An audible indicator 234 may include one or more speakers for generating audible sounds as indicators. The tactile indicator may include a vibrating component, oscillating component, or some other physical sensory tactile component.

The transceiver 237 may be a device for communicating data with other devices in the network environment 200 via wired communication, wireless communication, or some combination of the communication methods. The transceivers 237 may enable the feedback device 106 to be in data communication with the sensing system 103 and other device via the network 203.

The camera 240 can be used to capture images and/or video of a golfer executing a golf swing. The camera 240 can be used to detect particular movements of the golfer are executed in the predefined sequence. The camera 240 can be representative of one or more cameras. In some embodiments, the camera 240 can track the body movements of the golfer by tracking the movement of the leg sensing device 109 and/or the foot sensing device 107.

Also, various data are stored in a data store 243 that is accessible to the feedback device 106. The data stored in the data store 243 may include sensor data, feedback signal data, or other suitable data.

The feedback device 106 may be configured to execute various applications such as a feedback application 231 and/or other client applications. The feedback application 231 can be executed to collect sensor data from the sensing system 103, activate feedback indicators 234, and configure settings for the sensing system 103. Client applications may also be executed in a feedback device 106, for example, to access network content accessed over the network 203, thereby rendering a user interface on the display 118. To this end, client applications may comprise, for example, a browser, a dedicated application, etc., and the user interface may comprise a network page, an application screen, etc. The feedback device 106 may be configured to execute applications beyond the feedback application 231 and the client application such as, for example, media applications, social networking applications, video analysis applications, and/or other applications.

Next, a general description of the operation of the various components of the sensing system 103 and the feedback device 106 in the networked environment 200 is provided. To begin, a golfer initiates a golf swing after a set-up with proper posture, grip, and ball position. As a backswing is commenced, the heel of the Lead Foot lifts and triggers a foot sensor 204. The controller 210, via the transceiver 207a, transmits a first feedback signal to the feedback device 106. The feedback device 106 can activate a first feedback indicator 234 after receiving the first feedback signal.

As weight is transferred to the Trail Leg, the Trail Knee flexes or bends and triggers the leg sensing device 109, which causes leg sensing device to transmit a second feedback signal to the feedback device 106. The feedback device 106 can activate a second feedback indicator 234 if the first feedback signal is still active. The flexing of the Trail Knee permit coordinated activity of the quadriceps muscle of the Trail Leg and the gluteus muscles of the Trail Hip with upper body muscles in propelling the shoulder and body turn of the backswing and accommodates the transfer of weight to the Trail Leg and Hip, Trail Leg. This ensures stable vertical and lateral position of the lower body. The quadriceps and gluteus muscles accumulate energy for the eventual sequence of downswing events. Both heel and knee feedback signals remain active while the backswing is completed. Then, while both signals are activated, the heel of the Lead Foot moves downward, which triggers the foot sensing device 107 to transmit a third feedback signal to the feedback device 106. The feedback device 106 can activate a third feedback indicator 234 if both the second feedback signal and the first feedback signal are still active or active within a predefined time period.

The downward movement of the heel of the Lead Foot indicates that that balance of the golfer is being transferred forward to commence and lead the sequence of downswing events, i.e., hip turn forward, shoulder turn forward, arm swing, then hands. Thus, the activation of each feedback indicator 234 may provide verification that the golfer's lower body positions and movements have been made in the predefined sequence.

In another embodiment, the sensing system 103 can direct the feedback device 106 to activate one or more feedback indicators 234 after receiving the sensor data from the foot sensor 204 and the leg sensor 219. For example, the sensing system 103, via controller 210 and/or controller 225, can first determine that the heel of the Lead Foot has been raised and instruct the feedback device 106 to activate a first feedback indicator 234.

Next, as the knee is bent to a sufficient degree, the sensing system 103 can receive a second feedback signal from the leg sensing device 109. At this point, the sensing system 103 can determine if the first feedback signal is still active while the second feedback signal is active. If this is the case, the sensing system 103 can instruct the feedback device 106 to activate a second feedback indicator 234. Then, as the full backswing motion of the upper body is completed, the heel of the Lead Foot lowers and triggers the foot sensor 204. The sensing system 103 can determine if both the first feedback signal and the second feedback signal are still active or were active within a predefined time period. If this is the case, the sensing system 103 can instruct the feedback device 106 to activate a third feedback indicator 234. The third feedback indicator is the "go" signal for the train of downswing movement.

Feedback indicators 234 may be provided by the feedback device 106 to replace mental focus on hands, arms, or upper body movements (or avoidance of such movements). The various embodiments can teach awareness of physiological cues during the execution of the swing. This awareness facilitates learning the important role of coordinated activity of the lower body throughout the swing: backswing with balanced weight transfer and full shoulder turn, without lifting the Trail side of the body. This is followed by a downswing solely initiated by the solid ground contact of the Lead Foot and led by the Lead Leg and Hip to receive the transfer of weight forward.

The various embodiments of the present disclosure can be appropriate for use with or without the accompaniment of an instructor. Various embodiments can also be integrated with existing swing training devices which may use mechanical or electrical devices to record weight transfer during the golf swing or which may use video, GPS, or transponder devices to record body movements during the golf swing. In these non-limiting scenarios, the embodiments can provide valuable feedback signals during the execution of the swing thereby giving otherwise unavailable real-time indication of relevant physiological cues for learning. Additionally, the timing and synchronization of the signals can be controlled and varied to permit analysis and comparison of differential settings. In another example, threshold settings can be configured for the various sensors. For instance, a heel height can be set to represent a height at which a heel has to be lifted in order to trigger the threshold.

The various embodiments may transfer data to a dedicated or general communication or computing device. Software accompanying the embodiments allows the visualization and analysis of the timing and other dynamics of various steps of the process, in relation and response to the feedback signals. The software can also allow comparison of the user's data to pre-built templates that are either stored on the computing device or supplied through a communications connection from a central server. The software also stores and displays historical data from the user, in relation and response to the feedback signals, with comparative analyses against templates chosen either automatically by the software or by the user.

In another embodiment, the feedback device 106 and/or the sensing system 103 can allow a user to configure various settings associated with the feedback indicators 234, sensor settings, timer settings, and other suitable settings. For example, a setting user interface can be rendered that allows a user to select the type of feedback indicator 234. The setting user interface can also allow for sensor and timer settings to be configured to accommodate user preferences. For example, a golfer may want to adjust the sensor and timer settings to accommodate the unique features of his or her swing. For instance, a timer setting may be configured to set a time period for executing each stage of the swing. As an example, a time period may represent an amount of time to execute a full swing, a portion of a swing, and/or other suitable stages of a golf swing. Particularly, a time period can be set for a transition from a backswing to a downswing. In other words, if the golfer does not execute the transition from the backswing to the downswing within the time period, then a feedback indicator 234 may not be activated. For example, the time period may represent a time that a golfer has to transition from a state where the golfer's trailing knee is bent and the heel of the Lead Foot is up to another state of a downswing where the golfer's heel of the Lead Foot is being lowered.

In some embodiments, at least a portion of the sensing system 103 and/or the feedback device 106 can be implemented in a golf practice mat used in golf driving ranges and in residences. The golf practice mat may be a floor mat that includes a battery, a foot sensing device 107, and a feedback device 106. The foot sensing device 107 may be embedded within the floor mat and may comprise one or more pressure sensors. The pressure sensors can provide data that can be used to detect instances in which a heel of the foot has been lifted and lowered. The amount of pressure needed to trigger a heel being raised or lowered can be configured by the golfer.

Additionally, the golf practice mat embodiment may have the feedback device 106 attached to a far side of the floor mat where it is visible to the golfer. As a golfer executes a swing, the feedback device 106 can provide visual or audible indicators verifying a proper execution of each stage of the golf swing.

The golf practice mat may be in data communication with a leg sensing device 109, such as a knee brace, a knee strap, and other suitable devices that can be affixed to a leg of a golfer. The leg sensing device 109 may be in wired, wireless, or some combination of data communication with the golf practice mat.

Figure 3:
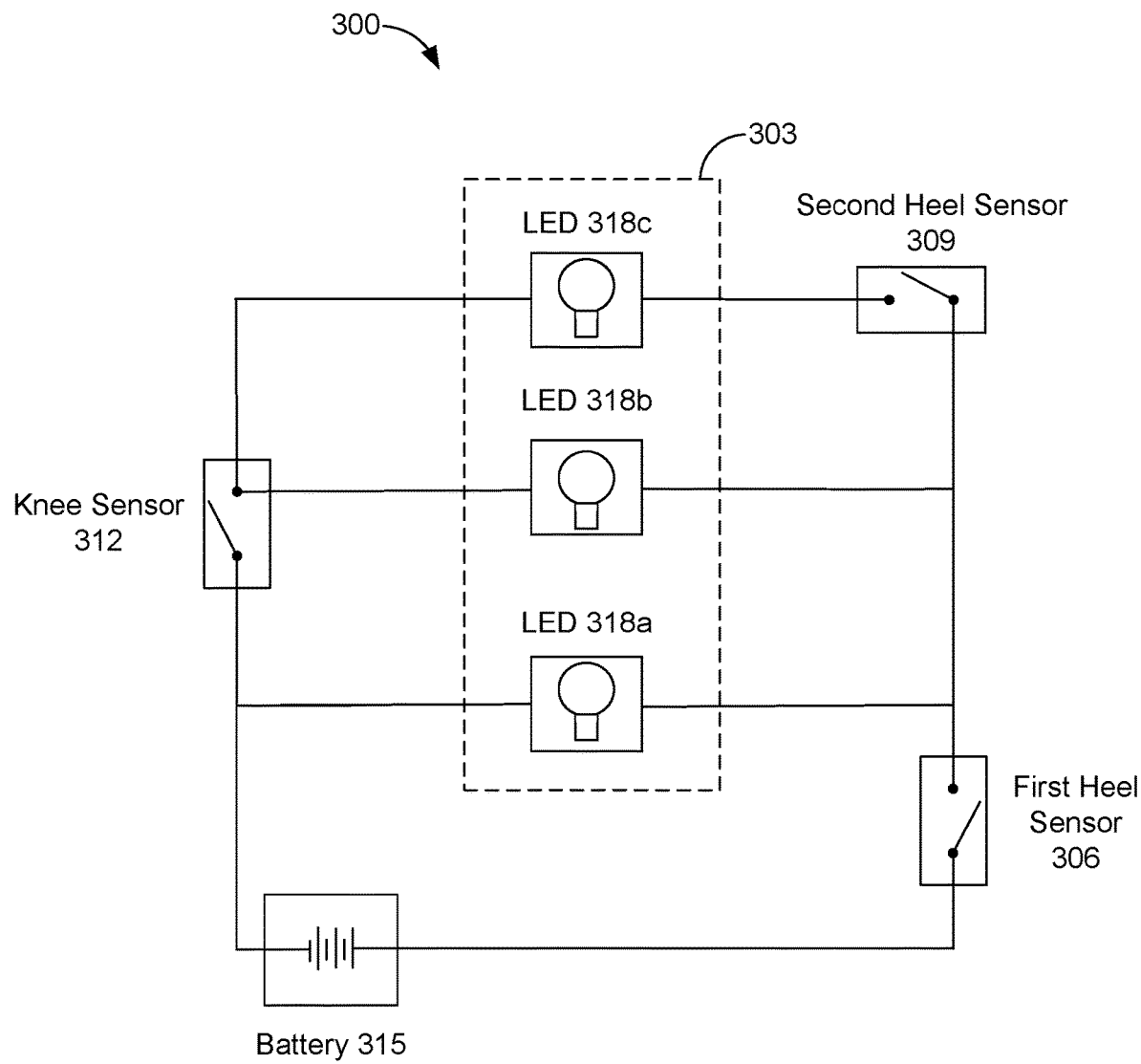
FIG. 3 illustrates a schematic drawing of another example feedback sensing system, according to an embodiment described herein.

With reference to FIG. 3, shown is a schematic of a feedback sensing system 300. In one embodiment, among others, the illustrated feedback sensing system 300 is a low-voltage electrical circuit. As shown in FIG. 3, the feedback sensing system 300 includes a feedback device 303 that is electrically coupled to a first heel sensor 306, a second heel sensor 309, a knee sensor 312, a battery 315, and other suitable electric components. The feedback device 303 includes a first light emitting diode (LED) 318a, a second LED 318b, and a third LED 318c (collectively LEDs 318).

The first heel sensor 306, the second heel sensor 309, and the knee sensor 312 are depicted as switches in FIG. 3 as one non-limiting example. The switches can open and close aspects of a circuit path, where closing a circuit path can permit the flow of current to activate a portion of the feedback sensing system 300. The first heel sensor 306 and the second heel sensor 309 can be attached in, on, or under the shoe of a golfer. The first heel sensor 306 and the second heel sensor 309 can also be embedded into clothing or another device worn on near the foot. The knee sensor 312 can be attached to a knee or any substantially near the knee of the golfer. The knee sensor 312 can also be embedded into clothing or another device worn on the body.

As shown in FIG. 3, the battery 315 is electrically coupled to a first heel sensor 306. The first heel sensor 306 is electrically coupled to the first LED 318a, the second LED 318b, and the second heel sensor 309. The second heel sensor 309 is electrically coupled to the third LED 318c, which is in turned electrically coupled to the knee sensor 312. The knee sensor 312 is also electrically coupled to the second LED 318b, the first LED 318a, and the battery 315.

In one aspect, the first heel sensor 306 closes the circuit path when the golfer lifts the heel of his or her shoe during a beginning of a backswing. By closing the circuit at the first heel sensor 306, current is permitted to flow from the battery 315 through the first heel sensor to the first LED 318a and back to the battery 315. By providing current to the first LED 318a, the first LED 318a is activated to illuminate as a first visual confirmation that the golfer properly lifted the heel.

Next, the feedback sensing system 300 can detect a shift in weight of the golfer from the Lead Foot to a back foot. The feedback sensing system 300 can detect the transfer in weight by detecting a certain amount of bend in the knee of the Trail Leg. At a certain point, the bend in the knee of the Trail Leg closes the circuit at the knee sensor 312. If the knee sensor 312 is closed and the first heel sensor 306 is closed, then the second LED 318b will be activated to illuminate as a second visual confirmation. The second visual confirmation indicates that the golfer has maintained a raised heel for the Lead Foot, detected by the first heel sensor 306, and sufficiently bent the Trailing Knee. If the golfer lowers the heel before the knee is bent, then the first heel sensor 306 opens the circuit and prevents the first LED 318a and the second LED 318b from being activated.

Next, at the peak of the backswing, the golfer transitions into a downswing. As the golfer begins the downswing, the golfer lowers the heel of the Lead Foot. The downward movement of the heel closes the circuit path by triggering the second heel sensor 309. If the first heel sensor 306 and the knee sensor 312 are also closed, then circuit flows from the first heel sensor 306 through the second heel sensor 309 to the third LED 318c, in which the current is permitted to flow through the knee sensor 312 and to the battery 315. Upon receiving current, the third LED 318 is activated. Thus, the second heel sensor 309 may be activated by the commencement of the lowering of the heel of the Lead Foot while the circuit is activated, i.e., before the Lead Foot comes completely down and while the trail knee remains detected as being bent, via the knee sensor 312, and the shoulders and arms remain in the backswing position relative to the lower body. The second heel sensor 309 can be coordinated with the first heel sensor 306 so that a portion of the circuit remains closed while first heel sensor 306 remains activated for a sufficient time to allow variation in the time of response to the third feedback signal. Thus, circuit arrangement can activate each of the LEDs 318 when a proper sequence of movements are detected by the golfer.

Figure 4:
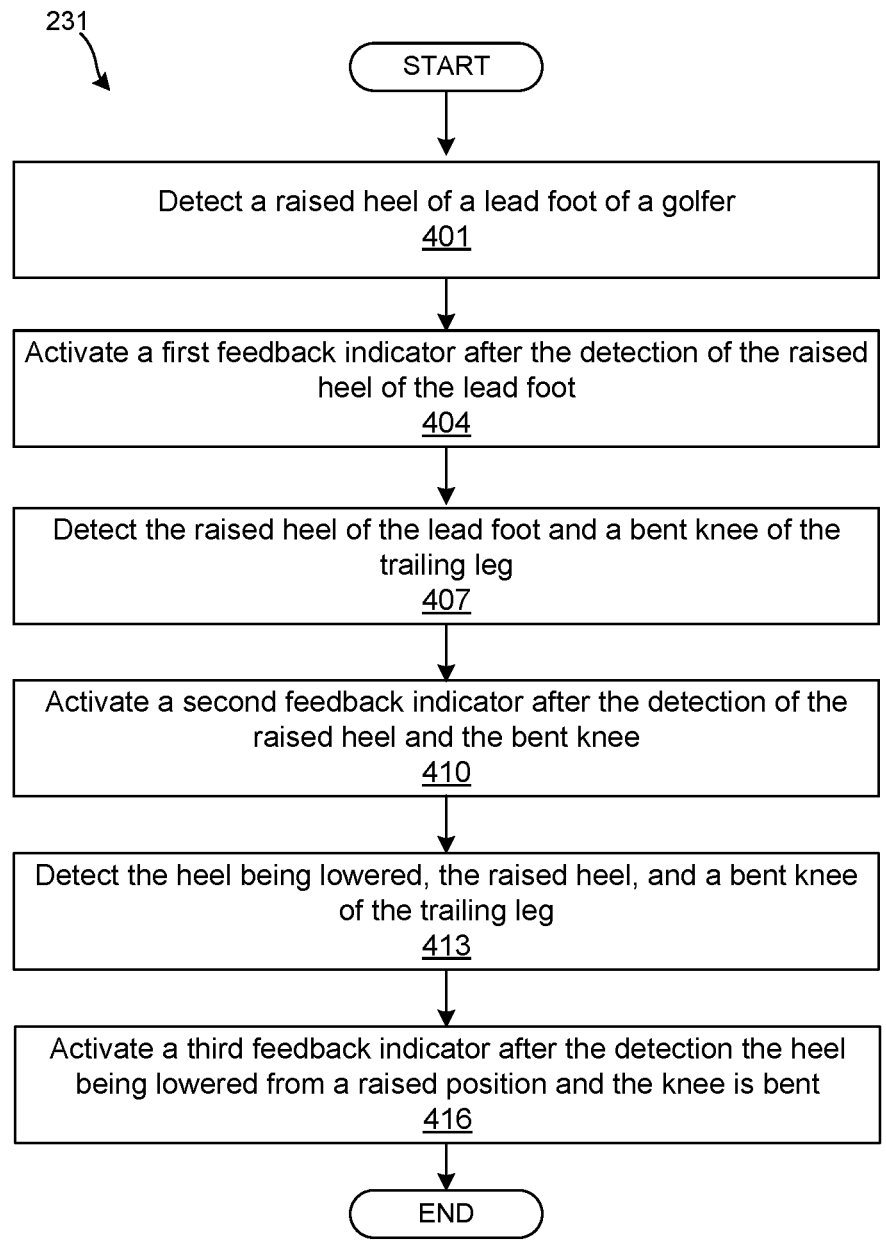
FIG. 4 is a flowchart illustrating one example of functionality implemented as portions of a swing application in the feedback system or the output device of FIG. 2, according to various embodiments of the present disclosure.

Referring next to FIG. 4, shown is a flowchart that provides one example of the operation of a portion of the feedback application 231 according to various embodiments. It is understood that the flowchart of FIG. 4 provides merely an example of the many different types of functional arrangements that may be employed to implement the operation of the portion of the feedback application 231 as described herein. As an alternative, the flowchart of FIG. 4 may be viewed as depicting an example of elements of a method implemented in the feedback device 106 (FIG. 2) according to one or more embodiments. In various embodiments, the flowchart of FIG. 4 may be executed in the sensing system 103 (FIG. 2), the feedback device 106, or a combination of the devices. In some embodiments, the feedback device 106 may include at least portion of the sensing system 103, such as the foot sensing device 107 (FIG. 2) or the leg sensing device 109 (FIG. 2). Alternatively, at least a portion of the feedback device 106 may be included in the sensing system 103.

Beginning with box 401, the feedback application 231 can receive a ready signal from a ready switch. The ready signal can place the feedback application 231 in a ready mode, which can represent that the golfer has addressed the golf ball and is ready to begin a golf swing. In some cases, the feedback sensing system 100 and/or the sensing system 103 may be powered off or in a standby mode. A power switch, a ready switch, or some other means may be used to power on the components. Alternatively, the power switch, the ready switch, or some other suitable means may be used to move the feedback sensing system 100 from the standby mode to a ready mode of operation.

As the golfer begins a swing, the feedback application 231 can determine or detect that a heel of a Lead Foot of a golfer has been lifted. The feedback application 231 can receive a feedback signal from the sensing system 103 which indicates that the foot sensor 204 (FIG. 2) has been triggered because a heel of a Lead Foot of the golfer has been raised. In some embodiments, the foot sensor 204 can detect that the heel of the Lead Foot of the golfer has been raised enough to meet or exceed a threshold. After detecting that the heel has met a threshold, the foot sensor 204 can communicate that a first state is active, which can be represented as a first feedback signal.

In box 404, the feedback application 231 can activate a first feedback indicator 234 (FIG. 2) in the feedback device 106 after the detection of the raised heel or after receiving an indication that a first state of the foot sensor 204 is active. In some embodiments, the feedback device 106 may be smartphone, a dedicated device, or incorporated into another device. The feedback indicator 234 may represent a first audible tone or a first visual indicator such as a first LED. In other cases, the feedback device 106 may be attached to a golfer in order to provide a physical indication, such as a vibration.

In box 407, the feedback application 231 can determine or detect that the heel of the Lead Foot is still lifted and that a knee of the Trail Leg is bent. The leg sensing device 109 can determine that the knee of the Trail leg is bent to such a degree to meet a threshold. The threshold can relate to a degree of bend at the knee. The threshold can be configured by the user at the sensing system 103 and/or the feedback device 106. Further, in some embodiments, the detection of the knee being bent can represent a second state. In some embodiments, the feedback application 231 may determine an instance in which both the first state and the second state are active contemporaneously.

In box 410, the feedback application 231 can activate a second feedback indicator 234 after the detection of the raised heel and the bent knee. If the heel of the Lead Foot comes down before the knee is bent, or the knee does not remain bent, then the second feedback indicator 234 is not activated. Accordingly, the sensing system 103 and/or the feedback device 106 can ensure that the detected movements occur in a predetermined sequence.

In box 413, the feedback application 231 can determine or detect that the heel of the Lead Foot is being lowered from a raised position and a knee of the Trail Leg is bent. The heel lowering from the raised position indicates that the sequence of downswing movements can begin, including weight shift forward. The detection of the heel lowering can involve determining that the heel has been lowered a threshold distance from the raised heel position. In other embodiments, the foot sensor 204 can be used to detect both the raising of the heel at a first instance and the lowering of the heel at a second instance. The foot sensor 204 can indicate that the detection of heel has been lifted as a first state, and the foot sensor 204 can indicate that the detection of the heel being lowered as a third state. In some embodiments, the feedback application 231 can contemporaneously or substantially contemporaneously detect an instance in which the first state, the second state, and the third state are all active.

In box 416, the feedback application 231 can activate a third feedback indicator after detecting the heel being lowered from a raised position and the knee being bent. At this point, the golfer completes the sequence of downswing movement and hits the ball. In some embodiments, after activating the third feedback indicator, the feedback application 231 may move to a standby mode, which can conserve power and ignore body movements unrelated to a golf swing. From the standby mode, the feedback application 231 can detect a manipulation of a ready switch and move to a ready mode. By being placed in the ready move, the feedback application 231 can move to box 401 in preparation for the detection of the first movements of the next golf swing. Thereafter, the feedback application 231 can proceed to the end.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A system for detecting a sequence of golf swing movements, comprising:
   a first foot sensor that attaches to a Lead Foot of a user, the first foot sensor activates a first state of a golf swing sequence based at least in part on a first detection of a heel of the Lead Foot being raised;
   a knee sensor that attaches to a Trail Leg of the user, the knee sensor activates a second state of the golf swing sequence based at least in part on a second detection of a bend in the Trail Leg at an instance after the activation of the first state;
   a second foot sensor that attaches to the Lead Foot of the user, the second foot sensor activates a third state of the golf swing sequence based at least in part on a third detection of the heel of the Lead Foot being lowered at an instance after the activation of the first state and the activation of the second state; and
   a feedback device that activates a first indicator after the activation of the first state, wherein the feedback device activates a second indicator after the activation of the first state and the activation of the second state, wherein the feedback device activates a third indicator after the activation of the first state, the activation of the second state, and the activation of the third state.

2. The system of claim 1, further comprising a battery that is electrically coupled to the first foot sensor and coupled to the feedback device, wherein the first foot sensor is electrically coupled to the feedback device.

3. The system of claim 2, wherein the knee sensor is electrically coupled to the battery and coupled to the feedback device, wherein the second foot sensor is electrically coupled to the feedback device and coupled to the first foot sensor.

4. The system of claim 1, wherein the second activation of the second state further comprises representing an instance in which both the first state and the second state are active contemporaneously.

5. The system of claim 1, wherein the activation of the third state further comprises representing an instance in which the first state, the second state, and the third state are active contemporaneously.

6. The system of claim 1, wherein at least one of the first foot sensor or the second foot sensor is embedded within a shoe.

7. The system of claim 1, wherein at least one of the first indicator, the second indicator, and the third indicator of the feedback device comprises at least one of an aural indicator, a visual indicator, or a tactile indicator.

8. The system of claim 1, wherein at least one of the first foot sensor or the second foot sensor comprises at least one of a position sensor, a momentary switch, a proximity sensor, a contact sensor, or a pressure sensor.

9. A system for detecting golf swing movements, comprising:
   a sensor that attaches to a Lead Foot of a user, the sensor activates a first state of a golf swing sequence based at least in part on a first detection of a heel of the Lead Foot being raised,
   a leg sensor that attaches to a Trail knee of the user activates a second state of the golf swing sequence based at least in part on a second detection of a bent knee of a Trail Leg of the user while the first state is activated;
   the sensor activates a third state of the golf swing sequence based at least in part on a third detection of the heel of the Lead Foot being lowered at an instance while the first state and the second state are activated; and
   a feedback device that activates a first feedback indicator in response to receipt of the first state from the sensor, wherein the feedback device activates a second feedback indicator in response to receipt of the first state from the sensor and in response to receipt of the second state from the leg sensor, the feedback device activates a third feedback indicator in response to receipt of the third state from the sensor and in response to receipt of the second state from the leg sensor.

10. The system of claim 9, wherein the feedback device comprises a wireless transceiver for receiving a wireless signal representing an indication of at least one of the first state, the indication of the second state, or the indication of the third state.

11. The system of claim 9, wherein the sensor is attached to a shoe or a sock of the user.

12. The system of claim 9, wherein the leg sensor is positioned in at least one of a knee brace, a knee support band, or an apparel item.

13. The system of claim 9, wherein the sensor is positioned in or on a floor mat.

14. The system of claim 9, wherein the leg sensor activates the second state based at least in part on a bent threshold, wherein the bent threshold represents a quantity of degrees of a bent knee.

15. The system of claim 9, wherein the activation of the first feedback indicator, the second feedback indicator, or the third feedback indicator further comprises the activation of at least one of a light emitting device, a speaker, or a vibrating device.

16. The system of claim 9, wherein the sensor is electrically coupled to a battery and a transceiver.

17. The system of claim 16, wherein the battery is electrically coupled to an energy harvesting device that generates electrical energy after being activated from motion or a mechanical force.

18. A method for detecting a sequence of golf swing movements, comprising:
   detecting, via at least one computing device, a first state of a golf swing sequence based at least in part on a detection of a heel of a Lead Foot of a user being raised by a sensor;
   activating, via the at least one computing device, a first feedback indicator in response to detecting the heel of the Lead Foot being raised;
   detecting, via the at least one computing device, a second state of the golf swing sequence based at least in part on a detection of a knee of a Trail Leg of the user being bent by a leg sensor;
   activating, via the at least one computing device, a second feedback indicator in response to detecting the heel of the Lead Foot being raised and in response to detecting the knee of the Trail Leg being bent;

detecting, via the at least one computing device, a third state of the golf swing sequence based at least in part on a detection of the heel of the Lead Foot of the user being lowered from a raised position by the sensor; and activating, via the at least one computing device, a third feedback indicator in response to detecting the heel of the Lead Foot being lowered and in response to detecting the knee of the Trail Leg being bent.

19. The method of claim 18, wherein detecting the heel of the Lead Foot being raised further comprises:

identifying, via the at least one computing device, a first orientation of the heel of the Lead Foot of the user in a first frame of a video;

identifying, via the at least one computing device, a second orientation of the heel of the Lead Foot of the user in a second frame of the video; and identifying, via the at least one computing device, in a displacement of the heel of the Lead Foot from the first frame to the second frame of the video based at least in part on a plurality of model frames representing a raised heel.

20. The method of claim 18, wherein detecting the knee of the Trail Leg being bent for the Trail Leg further comprises:

identifying, via the at least one computing device, a first orientation of the knee of the Trail Leg in a first frame of a video;

identifying, via the at least one computing device, a second orientation of the knee of the Trail Leg in a second frame of the video after detecting the heel of the Lead Foot being raised; and determining, via the at least one computing device, that a degree of bend at the knee of the Trail Leg for the second orientation meets a knee bend threshold.

\* \* \* \* \*